(12) United States Patent
Hyun

(10) Patent No.: US 10,327,864 B2
(45) Date of Patent: Jun. 25, 2019

(54) GUIDE PIN FOR DENTAL IMPLANT SURGERY

(71) Applicant: Young Keun Hyun, Seoul (KR)

(72) Inventor: Young Keun Hyun, Seoul (KR)

( * ) Notice: Subject to any disclaimer, the term of this patent is extended or adjusted under 35 U.S.C. 154(b) by 27 days.

(21) Appl. No.: 15/828,372

(22) Filed: Nov. 30, 2017

(65) Prior Publication Data

US 2018/0085190 A1    Mar. 29, 2018

Related U.S. Application Data

(63) Continuation of application No. PCT/KR2017/001942, filed on Feb. 22, 2017.

(30) Foreign Application Priority Data

Mar. 17, 2016  (KR) .................. 10-2016-0032135
Sep. 2, 2016   (KR) .................. 10-2016-0112921

(51) Int. Cl.
| | |
|---|---|
| *A61C 1/08* | (2006.01) |
| *A61C 3/02* | (2006.01) |
| *A61C 19/04* | (2006.01) |
| *A61C 8/00* | (2006.01) |
| *A61C 9/00* | (2006.01) |

(52) U.S. Cl.
CPC ............ *A61C 1/084* (2013.01); *A61C 3/02* (2013.01); *A61C 8/0089* (2013.01); *A61C 9/0033* (2013.01); *A61C 19/04* (2013.01)

(58) Field of Classification Search
CPC ... A61C 8/0019; A61C 8/0021; A61C 8/0031; A61C 8/0083; A61C 8/0089–0092; A61C 5/46; A61C 5/48; A61C 5/88

USPC .................................... 433/72, 75, 76, 196
See application file for complete search history.

(56) References Cited

U.S. PATENT DOCUMENTS

| | | | | |
|---|---|---|---|---|
| 1,417,236 A | * | 5/1922 | Evans ............. | A61C 5/40 33/513 |
| 3,815,243 A | * | 6/1974 | Eames ............. | A61C 5/88 433/149 |
| 4,571,180 A | * | 2/1986 | Kulick ............. | A61C 19/04 433/102 |
| 5,110,293 A | * | 5/1992 | Linkow ............ | A61C 8/0019 433/176 |

(Continued)

FOREIGN PATENT DOCUMENTS

| | | | | |
|---|---|---|---|---|
| DE | 4444305 A1 | * | 6/1996 | ............. A61C 5/80 |
| KR | 10-1586081 | | 1/2016 | |

OTHER PUBLICATIONS

Translation of DE 44 44 305.*

*Primary Examiner* — Wade Miles
*Assistant Examiner* — Matthew P Saunders
(74) *Attorney, Agent, or Firm* — JCIPRNET

(57) ABSTRACT

Provided is a guide pin for dental implant surgery, providing guidance so that a practitioner easily determines a location and angle of an alveolar bone of a patient when forming an implant hole in the alveolar bone to place an implant in the alveolar bone. By using the guide pin for dental implant surgery according to the inventive concept, a practitioner may perform the surgery by determining an accurate location and shape of the alveolar bone of the patient when drilling an implant hole in the alveolar bone, and thus, the success rate of the implant surgery may be increased.

7 Claims, 6 Drawing Sheets

(56) References Cited

U.S. PATENT DOCUMENTS

| | | | | |
|---|---|---|---|---|
| 5,193,999 | A * | 3/1993 | Staubli | A61C 8/0089 |
| | | | | 33/514 |
| 6,024,564 | A * | 2/2000 | Kesling | A61C 19/043 |
| | | | | 433/141 |
| 9,454,846 | B2 * | 9/2016 | Pesach | A61C 9/0033 |
| 2011/0008755 | A1 * | 1/2011 | Misch | A61C 8/0019 |
| | | | | 433/176 |
| 2012/0315597 | A1 * | 12/2012 | Rasperini | A61C 19/043 |
| | | | | 433/72 |
| 2014/0342311 | A1 * | 11/2014 | McDonald | A61C 5/88 |
| | | | | 433/138 |
| 2017/0296308 | A1 * | 10/2017 | Lee | A61C 8/0089 |

* cited by examiner

GUIDE PIN FOR DENTAL IMPLANT SURGERY

CROSS-REFERENCE TO RELATED APPLICATION

This application is a continuation application of the international PCT application serial no. PCT/KR2017/001942, filed on Feb. 22, 2017, which claims the priority benefit of Korean Patent Application No. 10-2016-0032135, filed on Mar. 17, 2016 and Korean Patent Application No. 10-2016-0112921, filed on Sep. 2, 2016, in the Korean Intellectual Property Office, the disclosure of which is incorporated herein in its entirety by reference.

BACKGROUND

1. Field

The inventive concept relates to a guide pin for dental implant surgery, and more particularly, to a guide pin for dental implant surgery, providing guidance so that a practitioner easily determines a location and angle of an alveolar bone of a patient when forming an implant hole in the alveolar bone to place an implant in the alveolar bone.

2. Description of the Related Art

In general, a dental implant consists of a fixture, an abutment, and a crown.

The fixture includes a male screw portion to be inserted into the alveolar of a person to support and fix the dental implant overall.

The abutment is mounted to be coupled to an upper portion of the fixture and exposed above the gum.

The crown is a type of prosthesis replacing a natural tooth, and is formed to fit with the abutment to be adhered and fixed to the abutment.

When carrying out an implant surgery as described above, first, an implant hole is formed to insert a fixture into the alveolar bone. To form an implant hole, first, the shape of the alveolar bone is determined based on an image of a site where the implant hole is to be formed, captured by using X-ray or computerized tomography (CT). A plan is set to form an implant hole based on the shape of the alveolar bone determined through X-ray or CT, and then the practitioner drills a hole (implant hole) into the alveolar bone of the patient by using a drill according to the plan. During the process in which the practitioner drills an implant hole into the alveolar bone of the patient, it is impossible or highly difficult to check an X-ray or CT image in real time. Moreover, as the alveolar bone is covered by the gum, even when the practitioner is cognizant of the shape of the alveolar bone, it is very difficult to form an implant hole at an accurate location and in an accurate direction by considering a three-dimensional shape and location of the alveolar bone in a real surgery. If the initial direction or location of the formed implant hole is incorrect, an implant hole may have to be drilled again, or if the implant hole is too large, the implant surgery may have to be performed after filling the alveolar bone with a dental cement. This delays the time for restoration of the patient and increases discomfort for the patient.

SUMMARY

Provided is a guide pin for dental implant surgery, providing guidance to enable a practitioner to determine the shape (location and direction) of the alveolar bone of a patient also while forming an implant hole in the alveolar bone by using a drill.

Additional aspects will be set forth in part in the description which follows and, in part, will be apparent from the description, or may be learned by practice of the presented embodiments.

According to an aspect of an embodiment, a guide pin for dental implant surgery includes: an insertion portion extending in a length direction so as to be poked and inserted between an alveolar bone and the gum; and a guide portion configured to be coupled to the insertion portion to be extended in the length direction so as to guide an inclination of the alveolar bone by being exposed outside the gum when the insertion portion is inserted between the alveolar bone and the gum, the guide portion comprising a bone contact portion that is closely contacted to the alveolar bone in a direction facing the alveolar bone and a periosteal contact portion that is convexly formed in a direction facing a periosteum of the gum.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

A guide pin for dental implant surgery according to the inventive concept will now be described more fully with reference to the accompanying drawings.

Figure 1:
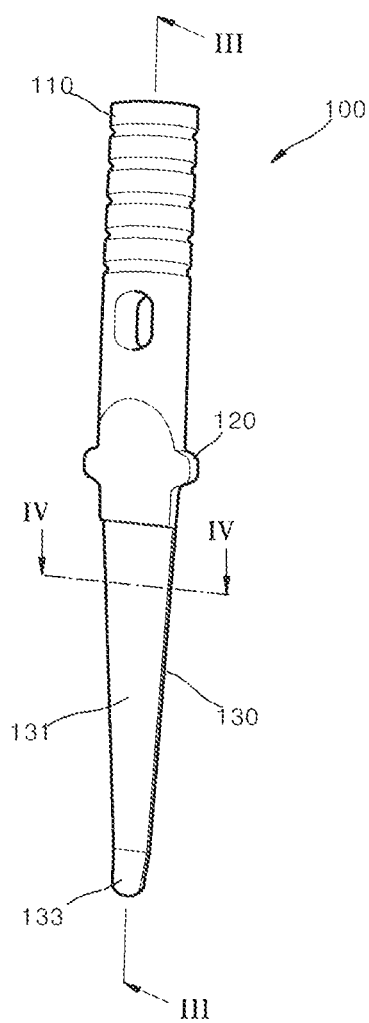
FIG. 1 is a perspective view of a guide pin for dental implant surgery according to a first example embodiment of the inventive concept.
Figure 2:
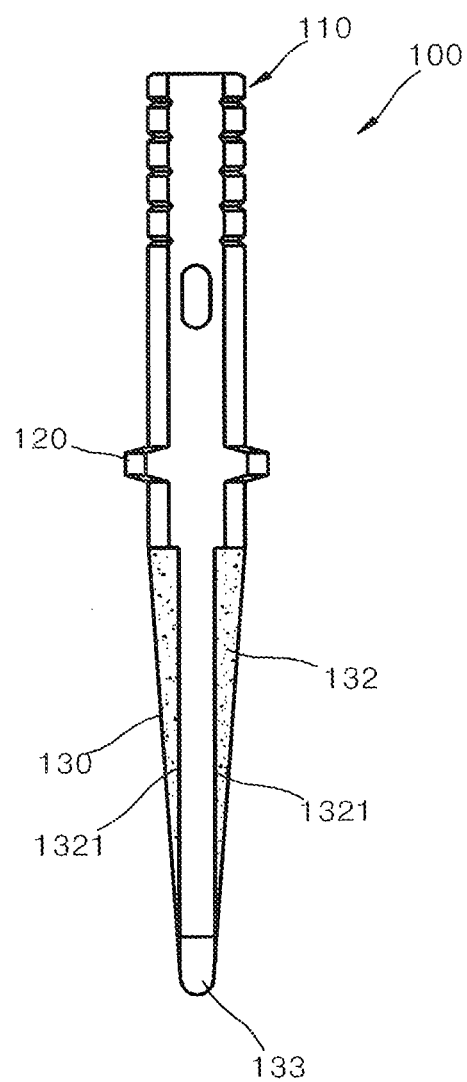
FIG. 2 is a rear view of the guide pin for dental implant surgery illustrated in FIG. 1.

FIG. 1 is a perspective view of a guide pin 100 for dental implant surgery according to a first example embodiment of the inventive concept. FIG. 2 is a rear view of the guide pin 100 for dental implant surgery illustrated in FIG. 1.

Referring to FIGS. 1 and 2, the guide pin 100 for dental implant surgery according to the first example embodiment of the inventive concept includes an insertion portion 130, a guide portion 110, and a support portion 120.

The guide portion 110 is formed in a rod shape extending in a length direction. The guide portion 110 is formed in a form that a practitioner may easily grasp using the finger or an additional tool. The guide portion 110 according to the present example embodiment has a cylindrical shape having a plurality of ring-shaped grooves formed on an outer circumference thereof.

The insertion portion 130 is coupled to a lower portion of the guide portion 110. The insertion portion 130 extends in a length direction so as to be poked and inserted between an alveolar bone 1 and a gum 2. When the insertion portion 130 is inserted between the alveolar bone 1 and the gum 2, the guide portion 110 is exposed outside, thereby guiding an inclination of the alveolar bone 1.

The insertion portion 130 includes a bone contact portion 131, a periosteal contact portion 132, and a curved portion 133.

As illustrated in FIG. 1, the bone contact portion 131 has a planar shape so as to be closely contacted to the alveolar bone 1 in a direction facing the alveolar bone 1. According to circumstances, the bone contact portion 131 may be formed concavely so as to correspond to the shape of an outer surface of the alveolar bone 1. A portion of the bone contact portion 131 facing the alveolar bone 1 may have a low surface roughness so that the portion is slid in close contact with the alveolar bone 1 when the insertion portion 130 is inserted between the alveolar bone 1 and the gum 2.

Figure 3:
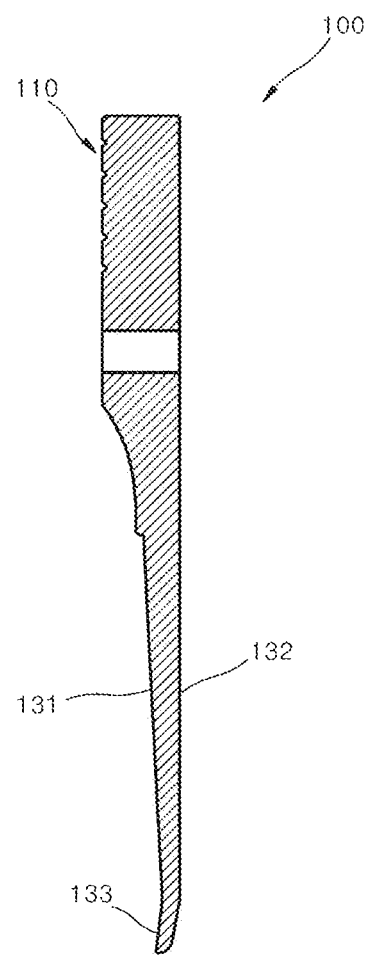
FIG. 3 is a cross-sectional view of the guide pin for dental implant surgery illustrated in FIG. 1 taken along line III-Ill.
Figure 4:
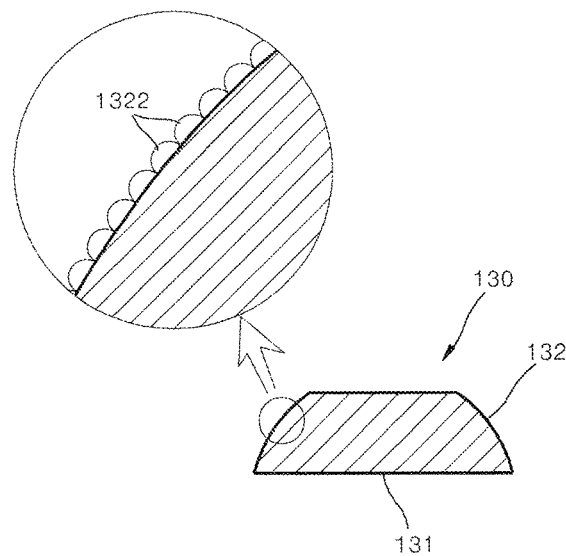
FIG. 4 is a cross-sectional view of the guide pin for dental implant surgery illustrated in FIG. 1 taken along line IV-IV.

The periosteal contact portion 132 is formed on a surface of the insertion portion 130 opposite to the bone contact portion 131. The periosteal contact portion 132 is formed convexly with respect to a direction facing the periosteum 3 of the gum 2. Referring to FIGS. 2 and 3, a protruding ridge 1321 of the periosteal contact portion 132 is formed to extend along an extension direction of the insertion portion 130. Here, the ridge 1321 is defined as a line connecting portions of the periosteal contacting portion 132 protruding at the highest heights. In the present example embodiment, the periosteal contacting portion 132 is convexly formed so that the ridge 1321 of the periosteal contacting portion 132 is formed along the extension direction of the insertion portion 130. Referring to FIG. 4, the periosteal contact portion 132 has a convex cross-sectional shape.

The periosteal contact portion 132 pushes the periosteum 3 and the gum 2 outwardly when the insertion portion 130 is inserted between the alveolar bone 1 and the periosteum 3 of the gum 2, thereby forming an entry path of the insertion unit 130. While the insertion portion 130 is inserted, the periosteal contact portion 132 is pressed and fixed by a restoring force of the gum 2 that has been pushed outwardly and tends to return to its original state. As both sides of the periosteal contact portion 132 having a convex shape, with respect to the ridge 1321, are pressed by the gum 2 based on the ridge 1321 of the periosteal contact portion 132 having a convex shape, shaking of the insertion portion 130 to the left and right may be prevented.

A plurality of protrusions 1322 may be formed on a portion of the periosteal contact portion 132. The protrusions 1322 may be formed by portions of the periosteal contact portion 132 to have a relatively high surface roughness than other portions. According to circumstances, the protrusions 1322 may be formed using an anodizing method. Referring to FIG. 2 and FIG. 4, the plurality of protrusions 1322 are formed from a half point to a two thirds point from an upper portion of the periosteal contact portion 132 in a downward direction. The plurality of protrusions 1322 formed on the portion of the periosteal contact portion 132 except a lower portion of the periosteal contact portion 132 may prevent the insertion portion 130 from shaking while the insertion portion 130 is inserted between the alveolar bone 1 and the periosteum 3.

Referring to FIGS. 1 and 3, the curved portion 133 is disposed at an end portion of the insertion portion 130. When the practitioner pushes the insertion portion 130 between the alveolar bone 1 and the gum 2 while holding the guide portion 110 with a hand or by using a tool such as forceps, the curved portion 133 separates the alveolar bone 1 and the gum 2. The curved portion 133 has a sharply curved shape bending at the end portion of the insertion portion 130 toward the bone contact portion 131. Due to the bent shape of the curved portion 133, the curved portion 133 helps the end portion of the insertion portion 130 maintain contact with the alveolar bone 1 when the insertion portion 130 is inserted between the alveolar bone 1 and the periosteum 3. The curved portion 133 having the above structure performs the function of accurately separating the alveolar bone 1 and the periosteum 3 of the gum 2. The curved portion 133 bent toward the bone contact portion 131 as described above guides an entry direction of the insertion portion 130 to face the alveolar bone 1 to thereby prevent the insertion portion 130 from poking the periosteum 3 or the gum 2.

The support portion 120 is formed to protrude in a connection portion between the insertion portion 130 and the guide portion 110. In the present example embodiment, the support portion 120 is formed to protrude in a direction perpendicular to the extension direction of the insertion portion 130 and the guide portion 110.

Hereinafter, the use and operation of the guide pin 100 for dental implant surgery according to the first example embodiment configured as described above will be described with reference to FIG. 5.

First, the practitioner holds the guide portion 110 by using the fingers or another tool. Next, the practitioner places the bone contact portion 131 of the insertion portion 130 to face the alveolar bone 1, and then locates an end of the curved portion 133 in a site where an implant hole is to be formed, and between the alveolar bone 1 and the gum 2.

Figure 5:
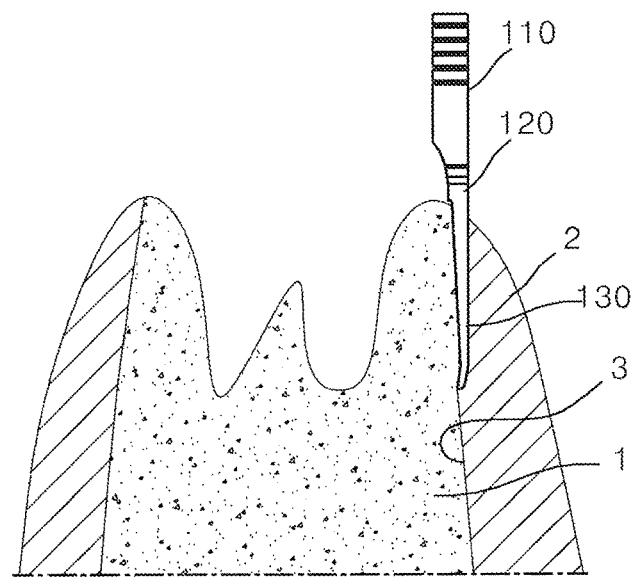
FIG. 5 illustrates how the guide pin for dental implant surgery illustrated in FIG. 1 is used.

In this state, the practitioner pushes the guide portion 110 downward to stick the curved portion 133 of the insertion portion 130 between the alveolar bone 1 and the gum 2 to be in a state as illustrated in FIG. 5. The insertion portion 130 is inserted between the alveolar bone 1 and the gum 2, and the support portion 120 is closely contacted to a surface of an upper end of the gum 2.

Here, the curved portion 133 is inserted between the alveolar bone 1 and the gum 2 while separating the alveolar bone 1 and the gum 2 from each other. As the curved portion 133 is bent toward the bone contact portion 131, the practitioner may effectively insert the curved portion 133 by sensing the curved portion 133 maintaining a contact state with the alveolar bone 1, through the guide portion 110.

When the insertion portion 130 is inserted between the alveolar bone 1 and the gum 2, the bone contact portion 131 contacts the alveolar bone 1 and the periosteal contact portion 132 contacts the periosteum 3 of the gum 2 as illustrated in FIG. 5. The protruding ridge 1321 of the periosteal contact portion 132 performs the functions of widening a gap with respect to the gum 2 to provide an entry path of the insertion portion 130 and holding the insertion portion 130 to prevent shaking of the insertion portion 130 to the left and right.

While the insertion portion 130 is inserted between the alveolar bone 1 and the gum 2 as described above, the guide portion 110 is in a protruded state according to the inclination of the alveolar bone 1 near the site where an implant hole is to be formed.

The practitioner may determine the shape and inclination of the alveolar bone 1 covered by the gum based on the location and the inclination of the guide portion 110 as described above, without using an image such as a computerized tomography (CT) image or an X-ray image. The practitioner may form an implant hole at an accurate location and in an accurate direction by referring to the location and direction of the guide portion 110 exposed to the outside.

According to circumstances, two guide pins 100 for dental implant surgery may be inserted into each of an inner portion and an outer portion of the alveolar bone 1. By using two guide pins 100 for dental implant surgery, a distance between the inner and outer portions of the alveolar bone 1 and the inclination of the inner and outer portions of the alveolar bone 1 may be determined effectively. By using this method, an implant hole may be formed in a more accurate location and direction.

When an implant hole is formed by using the guide pin 100 for dental implant surgery according to the inventive concept, the surgery may be performed by determining the shape of the alveolar bone 1 firsthand with the unaided eye during the surgery. According to this method, an implant hole may be formed with a remarkably higher accuracy than in the related art. As a result, the success rate of the dental implant surgery may be enhanced according to the inventive concept.

While the guide pin 100 for dental implant surgery according to the inventive concept has been described with reference to the first example embodiment above, the scope of the inventive concept is not limited to the example embodiment described above and illustrated in the drawings.

For example, a guide pin for dental implant surgery in which an indication line is marked on an outer surface of a guide portion may also be formed. By forming an indication line in parallel to an extension direction of the guide portion, the practitioner may better determine a degree of an inclination of the guide portion and refer to the degree of the inclination of the guide portion during the surgery. The indication line may be engraved or embossed in the guide portion or printed in a contrast color of that of the guide portion.

In addition, the structure and number of a support portion may be modified in various manners. A guide pin for dental implant surgery that includes only one support portion may also be formed.

In addition, the structures of the bone contact portion 131, the periosteal contact portion 132, and the curved portion 133 of the insertion portion 130 may be modified in other various forms different from those described above, and an insertion portion without the curved portion 133 may also be formed.

Figure 6:
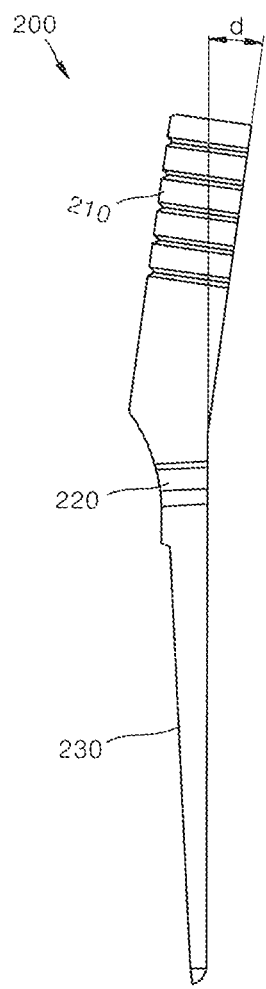
FIG. 6 is a side view of a guide pin for dental implant surgery according to a second example embodiment of the inventive concept.

In addition, while the guide pin 100 for dental implant surgery of the first example embodiment described above, in which the insertion portion 130 and the guide portion 110 are connected linearly, is illustrated, according to circumstances, a guide portion may be bent at an angle of about 3° to about 15° with respect to an insertion portion to be coupled to the insertion portion as illustrated in FIG. 6.

In addition, while the plurality of protrusions 1322 formed on a portion of the periosteal contact portion 132 are described above, a guide pin for dental implant surgery including a periosteal contact portion without the protrusions 1322 may also be configured.

FIG. 6 illustrates a guide pin for dental implant surgery according to a second example embodiment of the inventive concept.

A guide portion 210 according to the second example embodiment is different from the guide portion 110 of the first example embodiment in that the guide portion 210 is bent at a predetermined angle d with respect to an insertion portion 230 to be coupled to the insertion portion 230. In the second example embodiment, the guide portion 210 may be coupled to the insertion portion 230 preferably at an angle d of about 3° to about 15°.

When the guide portion 210 is bent toward the insertion portion 230 at an angle of about 3° to about 15°, even when the insertion portion 230 is inclined according to the inclination of the alveolar bone, the guide portion 210 may be in parallel to a direction in which an implant hole is formed or at a similar angle to that direction. In this case, the practitioner may easily determine the direction that the implant hole is formed, and moreover, the effect of preventing the guide portion 210 from interfering with a path of a drill used to form the implant hole may be obtained.

Figure 7:
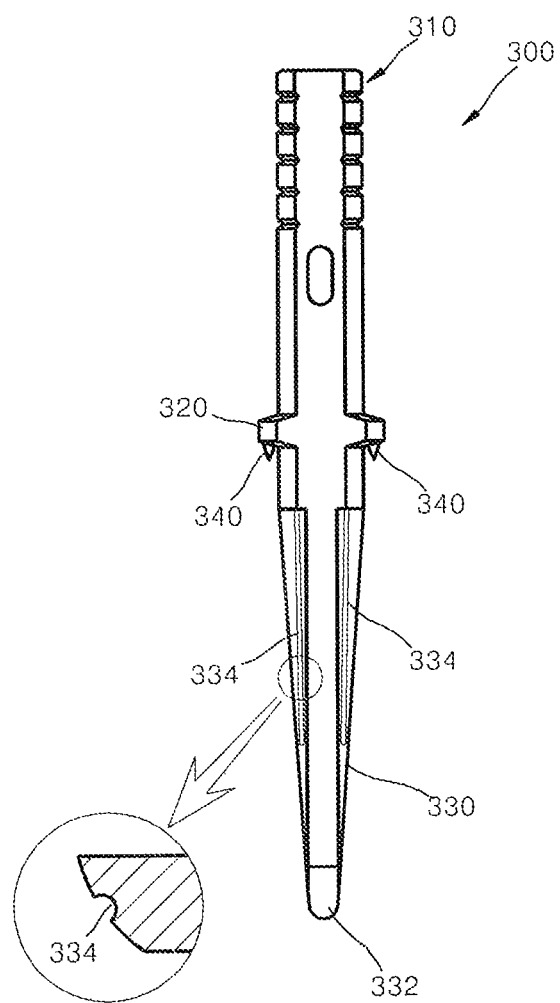
FIG. 7 is a rear view of a guide pin for dental implant surgery according to a third example embodiment of the inventive concept.

Next, a guide pin 300 for dental implant surgery according to a third example embodiment of the inventive concept will be described with reference to FIG. 7. FIG. 7 is a rear view of the guide pin 300 for dental implant surgery according to the third example embodiment of the inventive concept.

Referring to FIG. 7, the guide pin 300 for dental implant surgery according to the third example embodiment includes a guide portion 310, a support portion 320, and a pair of insertion portions 330.

Two fixing grooves 334 extending in a length direction of the insertion portions 330 are formed in a periosteal contact portion 332 of the insertion portions 330.

As a portion of the gum 2 is inserted into the fixing grooves 334 each formed on both sides of a ridge of the periosteal contact portion 332, shaking of the insertion portions 330 may be prevented more effectively.

An auxiliary insertion portion 340 is formed in the support portion 320 to protrude in a direction parallel to an extension direction of the insertion portions 330. The auxiliary insertion portion 340 is inserted between the alveolar bone 1 and the gum 2 when the insertion portions 330 are inserted between the alveolar bone 1 and the gum 2 to prevent shaking of the guide portion 310.

While the insertion portions 330 are inserted into the patient's gum 2, the support portion 320 is caught by an upper end of an interface between the tooth and the gum 2 to be supported by the gum 2, and the auxiliary support portion 340 supports the support portion 320 again against the gum 2, thereby preventing shaking of the guide portion 310.

By using the guide pin for dental implant surgery according to the inventive concept, a practitioner may perform the surgery by determining an accurate location and shape of the alveolar bone of the patient when drilling an implant hole in the alveolar bone, and thus, the success rate of the implant surgery may be increased.

What is claimed is:
1. A guide pin for dental implant surgery comprising:
an insertion portion extending in a length direction so as to be poked and inserted between an alveolar bone and a gum;
and a guide portion configured to be coupled to the insertion portion extended in the length direction, and configured to guide an inclination of the alveolar bone by being exposed outside the gum when the insertion portion is inserted between the alveolar bone and the gum,
wherein the insertion portion comprises a bone contact portion that is configured to closely contact the alveolar bone in a direction facing the alveolar bone and a periosteal contact portion that is convexly formed in a direction facing a periosteum of the gum, a support portion protruding in a connection portion between the insertion portion and the guide portion, and an auxiliary insertion portion protruding from the support portion in a direction parallel to the insertion portion so as to prevent shaking of the guide portion that is inserted between the alveolar bone and the gum.

2. The guide pin for dental implant surgery of claim 1, wherein the insertion portion further comprises a curved portion that is bent at an end portion of the insertion portion toward the bone contact portion so that the insertion portion is configured to be inserted between the alveolar bone and the gum by separating the alveolar bone and the gum.

3. The guide pin for dental implant surgery of claim 1, wherein a ridge protruding from the periosteal contact portion of the insertion portion extends along an extension direction of the insertion portion.

4. The guide pin for dental implant surgery of claim 3, wherein a plurality of protrusions are formed on at least a portion of the periosteal contact portion of the insertion portion.

5. The guide pin for dental implant surgery of claim 1, wherein the guide portion has a polygonal cross-section or includes a concave-convex portion surrounding an outer circumference of the guide portion so that the guide portion is easy to grasp.

6. The guide pin for dental implant surgery of claim 1, wherein at least one fixing groove extending in the length direction is formed in the insertion portion.

7. The guide pin for dental implant surgery of claim 1, wherein the guide portion is bent at an angle of about 3° to about 15° with respect to the insertion portion to be coupled to the insertion portion.

* * * * *